(12) United States Patent
Harrison

(10) Patent No.: US 11,525,806 B2
(45) Date of Patent: Dec. 13, 2022

(54) SENSOR PROBE FOR ANALYSIS OF A FLUID

(71) Applicant: SALUNDA LIMITED, Oxford (GB)

(72) Inventor: Martin Roy Harrison, Oxfordshire (GB)

(73) Assignee: SALUNDA LIMITED, Oxfordshire (GB)

( * ) Notice: Subject to any disclaimer, the term of this patent is extended or adjusted under 35 U.S.C. 154(b) by 207 days.

(21) Appl. No.: 17/043,938

(22) PCT Filed: Mar. 20, 2019

(86) PCT No.: PCT/GB2019/050780
§ 371 (c)(1),
(2) Date: Sep. 30, 2020

(87) PCT Pub. No.: WO2019/193315
PCT Pub. Date: Oct. 10, 2019

(65) Prior Publication Data
US 2021/0096101 A1    Apr. 1, 2021

(30) Foreign Application Priority Data

Apr. 4, 2018 (GB) ..................... 1805559

(51) Int. Cl.
*G01N 29/02* (2006.01)
*G01N 27/22* (2006.01)
(Continued)

(52) U.S. Cl.
CPC .......... *G01N 29/02* (2013.01); *G01N 27/221* (2013.01); *G01N 27/226* (2013.01);
(Continued)

(58) Field of Classification Search
CPC .... G01N 29/02; G01N 27/221; G01N 27/226; G01N 29/2437; G01N 33/2823
(Continued)

(56) References Cited

U.S. PATENT DOCUMENTS 3,999,443 A     12/1976  Appel et al.
7,135,870 B2 *  11/2006  Mohajer ................ G01R 27/22
                                                                324/698
(Continued)

FOREIGN PATENT DOCUMENTS

JP      S57135351 A     8/1982
WO      WO-2016179054 A1  11/2016
(Continued)

OTHER PUBLICATIONS

International Search Report for International Patent Application No. PCT/GB2019/050780, dated May 21, 2019.
(Continued)

*Primary Examiner* — Nimeshkumar D Patel
*Assistant Examiner* — Jean F Morello
(74) *Attorney, Agent, or Firm* — Marshall, Gerstein & Borun LLP

(57) ABSTRACT

A sensor probe for analysis of a fluid includes a base, and a pair of electrodes and a pair of shield members protruding from the base for insertion into the fluid. The electrodes have electrical oscillations generated therein for measurement of electromagnetic properties of the fluid, such as permittivity. The shield members are disposed outside the electrodes and have a dual purpose of electromagnetically shielding the electrodes and having vibrations generated therein for measurement of physical parameters of the fluid, such as density or viscosity. Thus, the single sensor probe can provide measurements of both electromagnetic properties and physical properties of the fluid.

23 Claims, 7 Drawing Sheets

(51) Int. Cl.
  G01N 29/24 (2006.01)
  G01N 33/28 (2006.01)
(52) U.S. Cl.
  CPC ..... G01N 29/2437 (2013.01); G01N 33/2823 (2013.01); *G01N 2291/0226* (2013.01); *G01N 2291/106* (2013.01)
(58) Field of Classification Search
  USPC .......................................................... 73/64.53
  See application file for complete search history.

(56) References Cited

U.S. PATENT DOCUMENTS

| | | | |
|---|---|---|---|
| 7,474,971 B2 * | 1/2009 | Hu | G01N 27/026 702/50 |
| 9,567,561 B2 | 2/2017 | Ossart | |
| 2004/0231402 A1 | 11/2004 | Eisenschmid et al. | |
| 2009/0120169 A1 | 5/2009 | Chandler, Jr. et al. | |

FOREIGN PATENT DOCUMENTS

| WO | WO-2017017076 A1 | 2/2017 |
|---|---|---|
| WO | WO-2017108280 A1 | 6/2017 |

OTHER PUBLICATIONS

Written Opinion for International Patent Application No. PCT/GB2019/050780, dated May 21, 2019.

Gregory and Clarke, "Tables of the Complex Permittivity of Dielectric Reference Liquids at frequencies up to 5GHz", National Physical laboratory Report MAT Jan. 23, 2012.

Heinisch et al., "Reduced order models for Resonant Viscosity and Mass Density Sensors", Sensors and Actuators A: Physical, vol. 220, Dec. 1, 2014, pp. 76-84.

* cited by examiner

SENSOR PROBE FOR ANALYSIS OF A FLUID

CROSS-REFERENCE TO RELATED APPLICATIONS

This is the United States national phase of International Patent Application No. PCT/GB2019/050780, filed Mar. 20, 2019, which claims priority to GB Application No. 1805559.0, filed on Apr. 4, 2018, the entire contents of each of which being hereby incorporated by reference herein.

FIELD OF THE DISCLOSURE

The present invention relates to sensor probes for analysis of a fluid.

BACKGROUND

Sensor probes may be used to analyse a range of fluids. Some non-limitative examples of fluids to which the invention relates are as follows.

In a case of particular interest, the fluid may be an oil-based drilling mud. Drilling muds typically consist of a mixture of oil (for example a synthetic base oil or diesel), brine (typically containing calcium chloride or sodium chloride), and solid materials such as clays and drilling rock, and so have a complex composition that is difficult to analyse. However, analysis may be performed by using an electromagnetic (EM) sensor probe to measure EM properties of the fluid such as permittivity. In the case of an oil-based drilling mud, the key feature as far as the electrical properties are concerned is that the oil forms the continuous matrix within which isolated brine droplets and isolated solid particles are dispersed. This type of mud exhibits a very low electrical conductivity at DC.

In another case, the fluid may be a water-based drilling mud where the brine forms the continuous matrix within which isolated oil droplets and isolated solid particles are dispersed. This type of mud exhibits a high electrical conductivity at DC, once electrode polarization effects are accounted for.

The complex electrical permittivity of an oil-based mud can be determined by passing an alternating current between an EM sensor probe comprising two electrodes immersed in the fluid and passing the same current through a reference resistor. The phase and amplitude of the voltage across the fluid are determined relative to the phase and amplitude of the voltage developed across the reference resistor. By analysing the change in phase and amplitude, it is possible to derive the capacitance and resistance of the sample and hence derive the real and imaginary parts of the complex permittivity of the fluid. This is a widely used technique which can be used to determine the permittivity over a wide range of frequencies, for example from 1 Hz to 100 MHz.

Analysis of other properties of a fluid, either oil-based or water-based, may also be performed. For example, density may be determined from measurements of the volume and mass of a sample. In another example, properties such as density and certain viscosity properties can be determined by immersing the tines of a tuning fork in the fluid, vibrating the tines and measuring parameters of the vibrations, for example the resonance frequency and/or the quality factor (Q factor). The resonance frequency decreases as the fluid density increases, and vice versa. By calibration of the tuning fork in a range of fluids with known densities, it is possible to determine the density of any fluid from the resonance frequency. In addition, the Q decreases as the fluid viscosity increases, and vice versa, so the Q factor of the tuning fork resonance can similarly be used to derive information on the viscosity of the fluid.

It is therefore possible to measure EM properties of a fluid using an EM sensor probe inserted into a sample of the fluid, and before or after that to measure the density of the same fluid, so that the results can be combined.

The present invention is concerned with improving such analysis of fluids.

GENERAL DESCRIPTION

According to the present invention, there is provided a sensor probe comprising a base, and a pair of electrodes and a pair of shield members protruding from the base for insertion into a fluid, the electrodes being capable of having electrical oscillations generated therein for measurement of EM properties of a fluid surrounding the electrodes and the shield members being disposed outside the electrodes for electromagnetically shielding the electrodes and being capable of having vibrations generated therein for measurement of at least one physical property of the fluid.

Thus, as in known sensor probes, electrodes are provided for making measurements of EM properties of oil-based muds such as complex permittivity over wide frequency range, for example from below 1 Hz to above 100 MHz. This is also suitable for taking measurements of fluids such as water-based muds which have a relatively high direct current (DC) electrical conductivity, but the results obtained at frequencies less than 1 MHz will be affected by electrode polarization effects.

However, the sensor probe is further adapted to include shield members disposed outside the electrodes that provide EM shielding of the electrodes and are also capable operating as a tuning fork by having vibrations generated therein which may be used for measurement of physical parameters of the fluid, such as density or viscosity. Thus, this design of the shielding members to have a dual purpose of both EM shielding and measurement of physical parameters means that the sensor probe can be used to make both measurements of both EM properties such as permittivity and physical properties such as density or viscosity.

The sensor probe is suitable for analysing a range of fluids, but has particularly suitability for a fluid that is an oil-based drilling mud. In that case, the information on EM properties and physical parameters can be used to determine the mud composition in terms of its oil, brine and solids content. However, the probe is capable of measuring the complex electrical permittivity and density of a much wider range of fluids with a low DC electrical conductivity.

The shield members are disposed outside the electrodes for providing EM shielding of the electrodes. Typically, the shield members have a greater lateral extent than the electrodes and protrude from the base at least as far as the electrodes. The shield members are also designed to have vibrations generated therein for measurement of at least one physical property of the fluid. The shield members are configured to have a mechanical resonance suitable for measuring the desired physical properties of the fluid. For example, in the case that the fluid is an oil-based drilling mud, the mechanical resonance frequency may typically be in the range from a lower limit that may be 10 Hz, or preferably 100 Hz to an upper limit that may be 10 kHz or preferably 1 kHz (regardless of the lower limit).

The base may have mass selected to control the vibration characteristics of the shield elements. Similarly, the shield members may be connected to the base by a portion having a smaller cross-sectional area than the shield members themselves for the purpose of reducing vibrational coupling between the base and the shield members.

The electrodes may be connected to the base by a piece of electrically insulating material. Besides providing electrical insulation, this material may be designed to reduce vibrational coupling between the shield members and the electrodes.

In use, the electrodes and shield members may be inserted into the fluid, and the sensor probe is used by both generating electrical oscillations in the electrodes and taking a measurement of at least one EM property of the fluid from the generated electrical oscillations, and vibrating the shield members and taking a measurement of at least one physical property of the fluid from the generated vibrations. These steps to measure at least one EM property and at least one physical property can be made simultaneously without any significant degradation in the quality of the measurements. This is not only convenient but also ensures that the measurements relate to the same sample of the fluid with the same composition and so may be reliably considered or combined together. This improves the accuracy of further analysis of the fluid performed on the basis of the measurements.

The sensor probe may be used to measure a fluid in a range of test environments.

In one example, the sensor probe may measure a static sample of fluid, for example a sample that has been extracted from an oil and gas operation for testing. In that case the electrodes and shield members may be inserted into the static sample of the fluid. For example, the fluid may be in a test pot, in which case the base of the sensor probe may be designed to fit the opening of the test pot.

In another example, the sensor probe may measure a flowing fluid, for example in a conduit such as a pipe. In that case, the electrodes and shield members may be inserted into the interior of the conduit where the fluid is flowing. The conduit may have an opening for permitting such insertion, in which case the base of the sensor probe may be designed to fit the opening.

In the case of a flowing fluid, the provision of EM shielding by a pair of shield members has the additional advantage of improving the flow of fluid past the sensor probe with minimal obstruction of the cross-section of the conduit. To further minimise the obstruction, the sensor probe may be inserted with a gap between the shield members arranged in line with the direction of flow of the fluid.

The sensor probe may further comprise a transducer arrangement comprising at least one transducer arranged to generate vibrations in the shield members and to convert the generated vibrations into a detection signal. Such a transducer arrangement may include a first transducer arranged to generate vibrations in the shield members and a second transducer arranged to convert the generated vibrations into a detection signal. Although a single transducer could be used for both purposes, the use of two transducers improves the quality of the signal to be processed.

The at least one transducer may be a piezoelectric transducer.

The at least one transducer may be connected between the pair of shield members. For example, the shield members may have rear portions extending rearwardly of a surface of the base from which the pair of shield members protrude, in which case the at least one transducer may be connected between the rear portions of the shield members. Connecting the at least one transducer between the pair of shield members has been found to improve the coupling efficiency of vibrations between the at least one transducer and the shield members.

The sensor probe may be provided with the following circuits.

For use with the shield members, the sensor probe may further comprise a vibration drive circuit connected to the transducer arrangement and arranged to supply a vibration drive signal thereto, and a vibration detection circuit connected to the transducer arrangement and arranged to detect one or more parameters of the generated vibrations from the detection signal.

One of the benefits of the sensor probe is that the vibration of the shield members also reduces the build-up of any material deposits on the surfaces of the sensor probe. This is a particular benefit when the probe is permanently inserted in a conduit or a container. To further enhance this effect of removing material deposits from the sensor probe, the shield members may periodically be vibrated with greater energy, for example by means of the vibration drive circuit supplying a cleaning drive signal of greater power than the vibration drive signal.

For use with the electrodes, the sensor probe may further comprise an oscillation circuit connected to the electrodes and arranged to supply an oscillation signal for generating electrical oscillations between the electrodes, and an oscillation detection circuit arranged to detect one or more parameters of the generated electrical oscillations.

To provide for simultaneous measurement of the at least one EM property and the at least one physical property, the oscillation drive circuit may be arranged to supply the oscillation signal to the electrodes at the same time as the vibration drive circuit supplies the vibration drive signal to the transducer arrangement.

Simultaneous operation of the shield members and the electrodes may be used to provide a further benefit by the oscillation detection circuit detecting the one or more parameters of the generated electrical oscillations synchronously with the vibration drive signal. Such a synchronous detection can provide a considerable improvement to the sensitivity of the measurement over a non-synchronous measurement providing a resulting improvement in the signal-to-noise ratio, as a result of the vibration induced in the electrodes having the effect of modulating the electrical response of the electrodes.

The sensor probe may further comprise an analysis system that is supplied with the one or more parameters of the generated vibrations and arranged to derive a measure of at least one physical property of the fluid therefrom, as well as being supplied with the one or more parameters of the generated electrical oscillations and arranged to derive a measure of at least one EM property of the fluid therefrom.

BRIEF DESCRIPTION OF THE DRAWINGS

To allow better understanding, an embodiment of the present invention will now be described by way of non-limitative example with reference to the accompanying drawings, in which.

DETAILED DESCRIPTION

Figure 1:
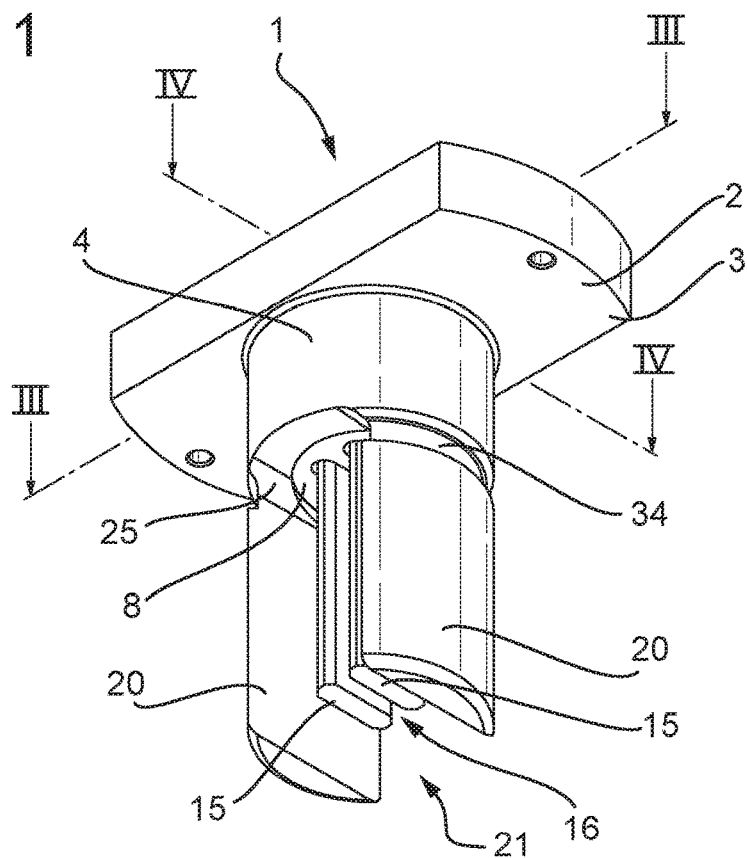
FIG. 1 is a perspective view from below of a sensor probe.
Figure 2:
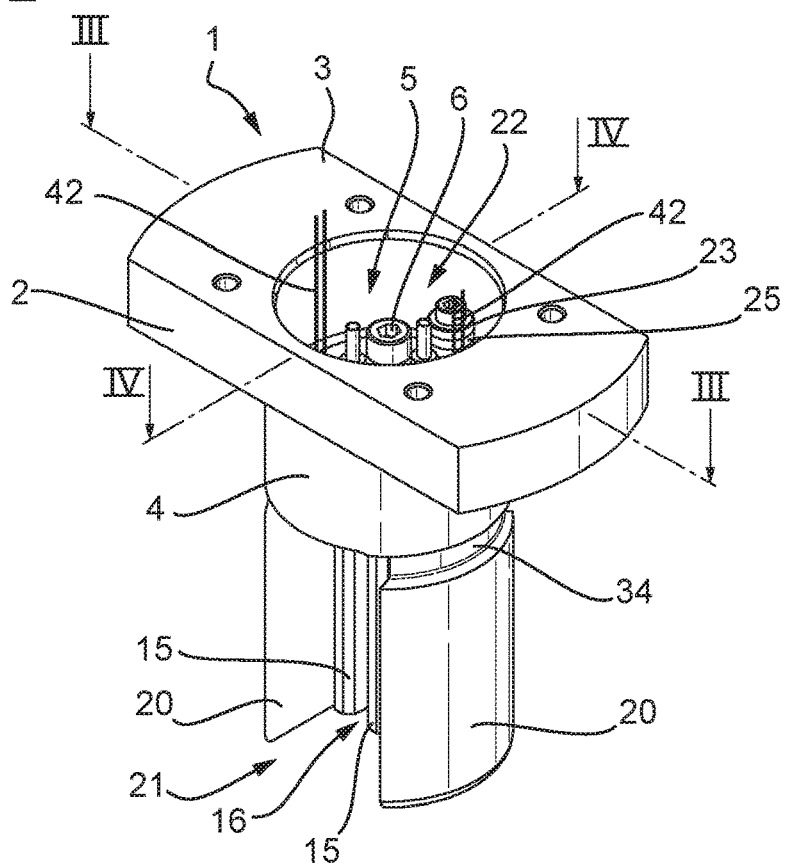
FIG. 2 is a perspective view from above of the sensor probe of FIG. 1.
Figure 3:
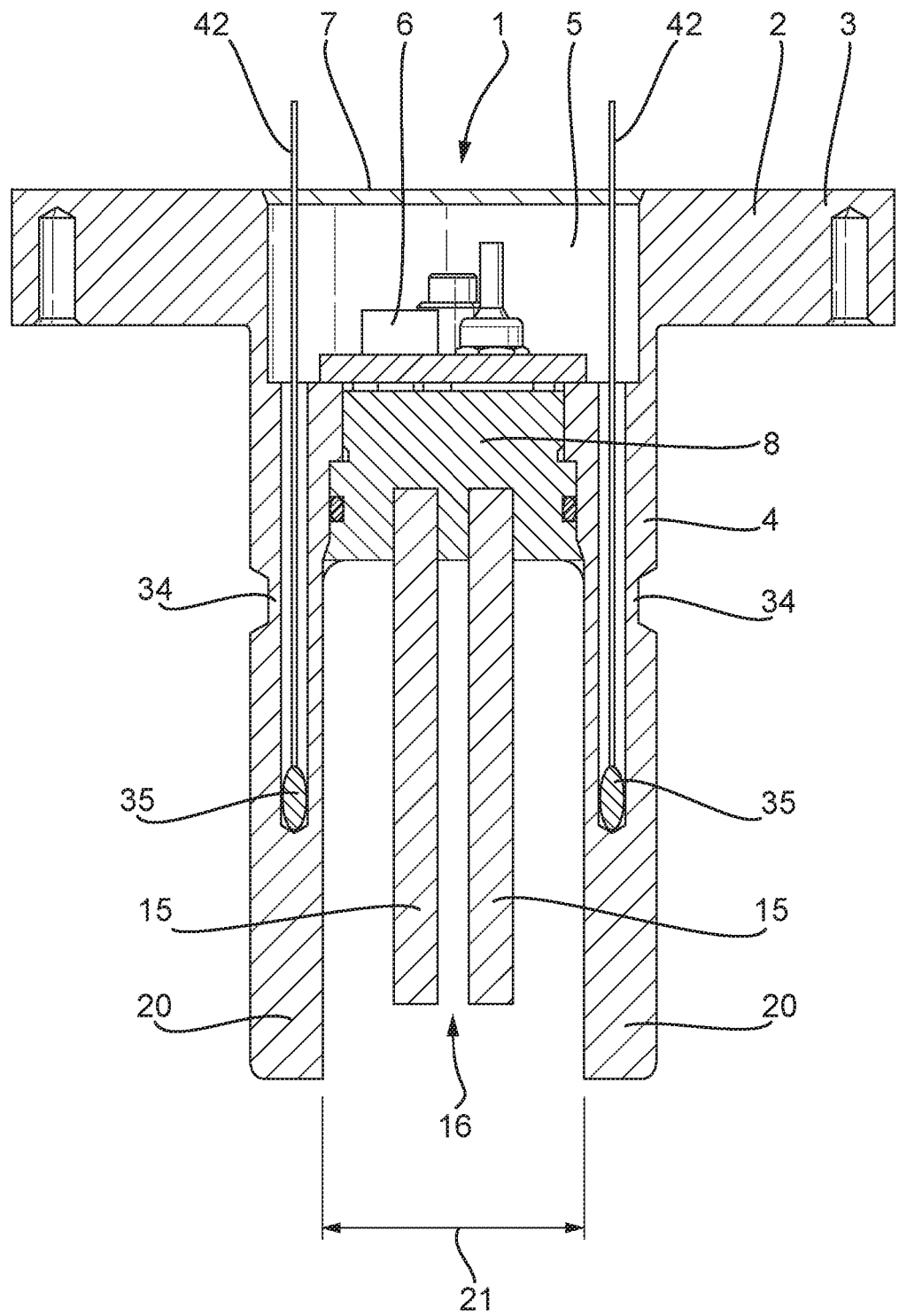
FIGS. 3 and 4 are cross-sectional views of the sensor probe of FIG. 1, the cross-section being taken along lines III-III and IV-IV, respectively, in FIGS. 1 and 2.
Figure 4:
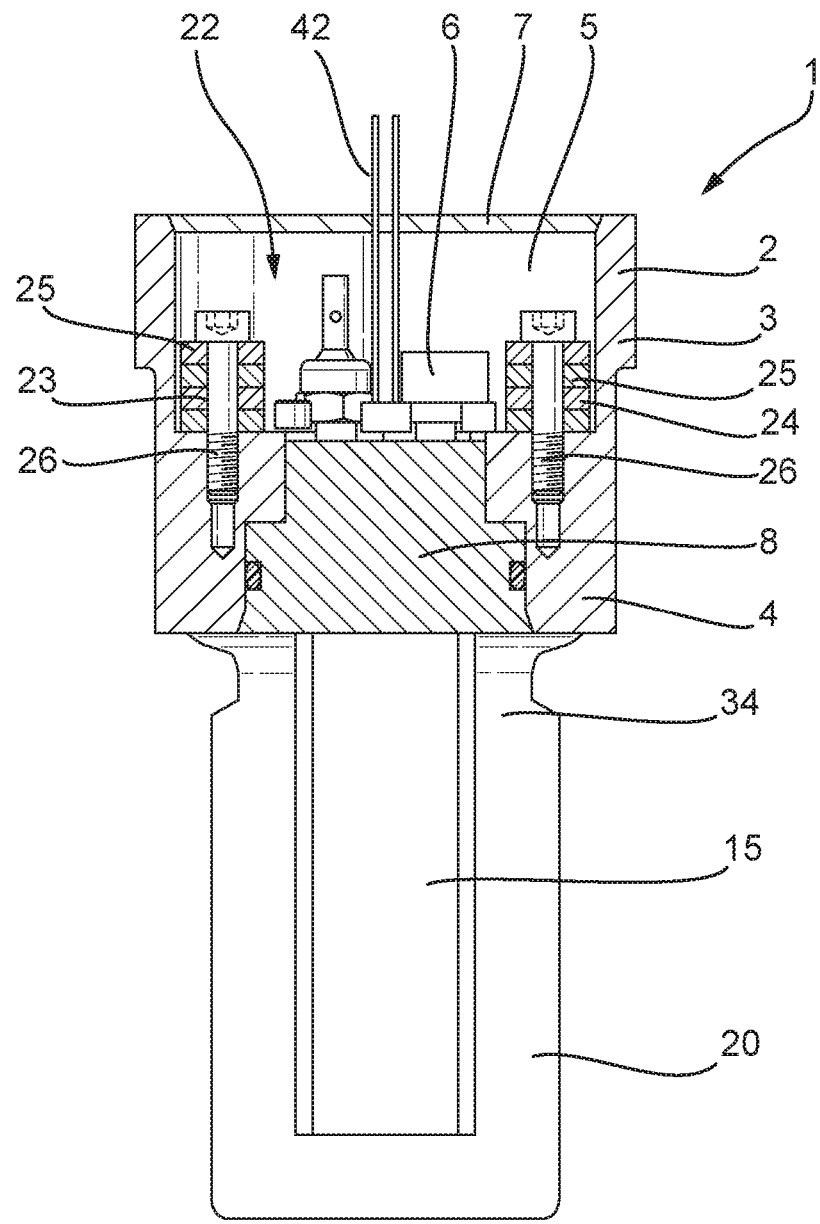
Figure 5:
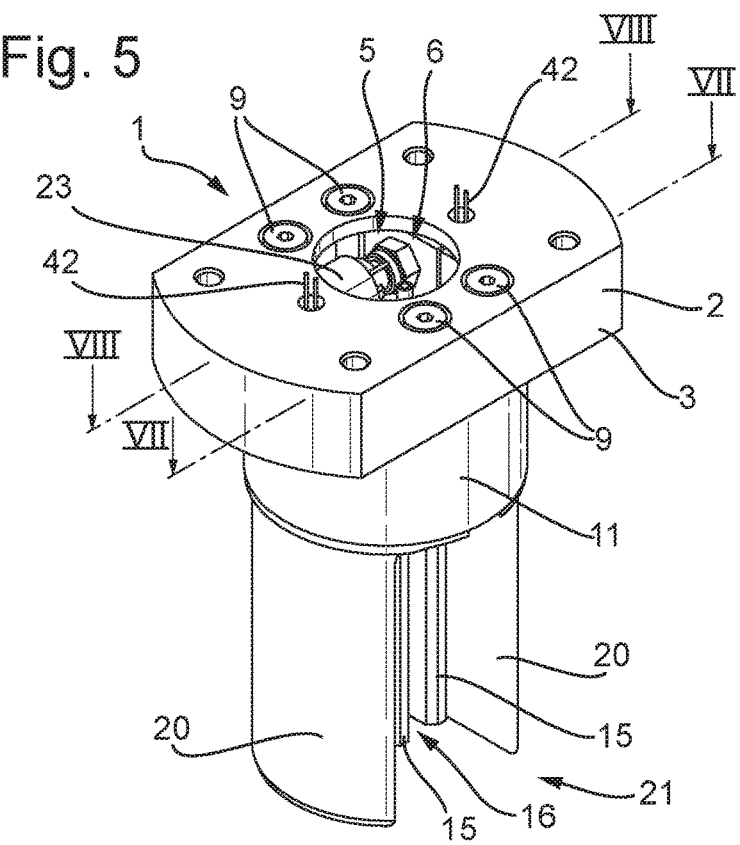
FIG. 5 is a perspective view from above of the sensor probe having a modified construction.
Figure 6:
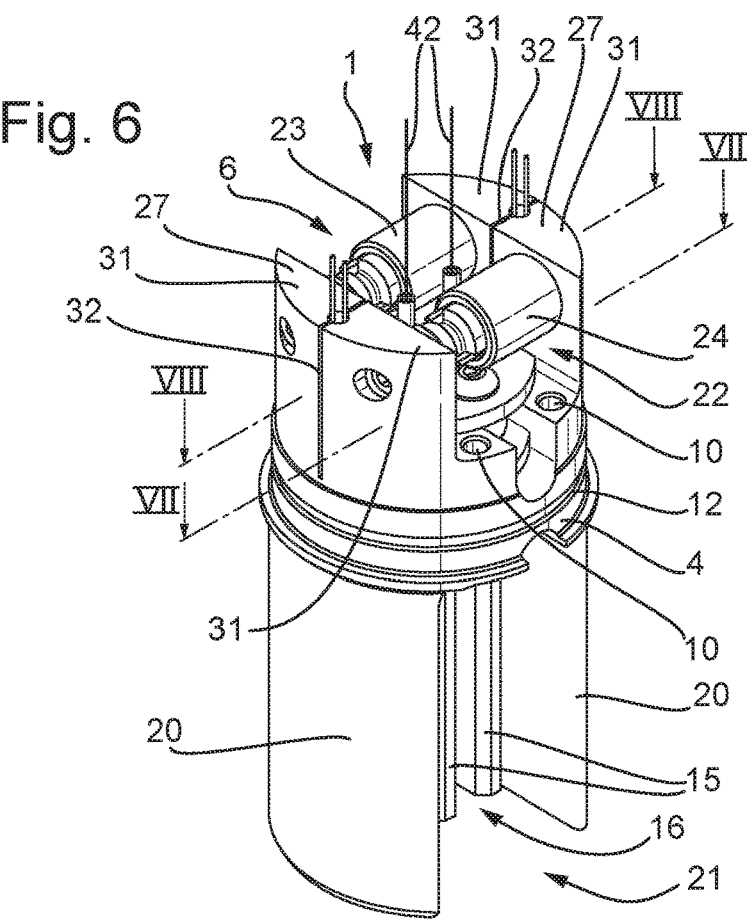
FIG. 6 is a perspective view from above of the sensor probe of FIG. 5 without a mounting plate and support ring.
Figure 7:
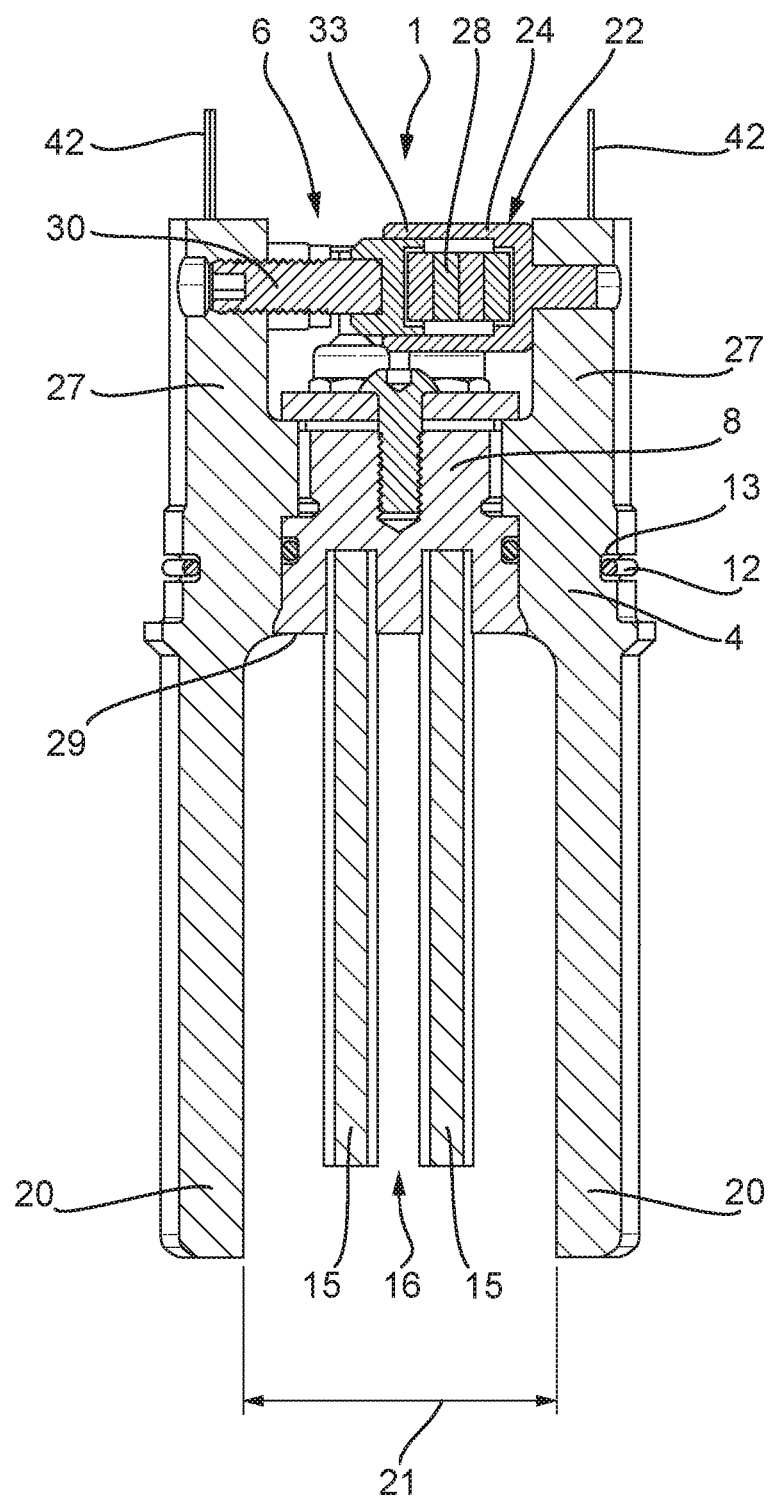
FIGS. 7 and 8 are cross-sectional views of the sensor probe of FIG. 6 without the mounting plate and support ring, the cross-section being taken along lines VII-VII and VIII-VIII, respectively, in FIGS. 5 and 6.
Figure 8:
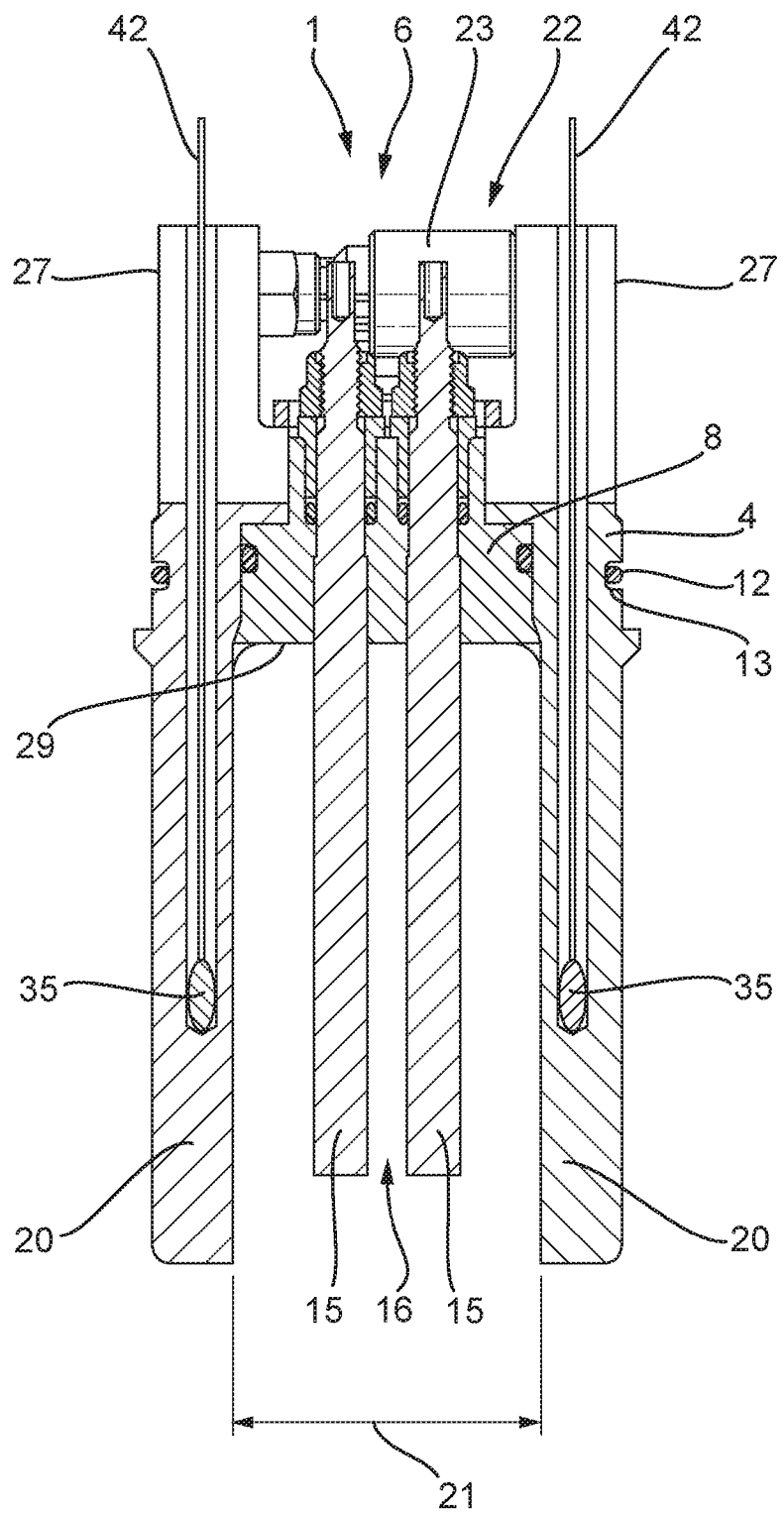

A sensor probe 1 is illustrated in FIGS. 1 to 4 and arranged as follows.

The sensor probe 1 has a base 2 that comprises a flat mounting plate 3 and a mounting ring 4 integrally formed with the mounting plate 3 and protruding therefrom. The base 2 is formed from metal, typically a stainless steel. Behind the mounting ring 4, the mounting plate 3 has a recess 5 which houses various electronic components 6 as described below. The recess 5 has a screen 7 extending across its opening to enclose the electronic components 6.

The mounting plate 3 serves several purposes.

Firstly, the mounting plate 3 provides a convenient support for attaching a screened enclosure 41 (shown in FIG. 9) to the top of the sensor probe 1 containing an electrical circuit 40 needed to obtain measurements.

Secondly, the mounting plate 3 may be designed to fit with a container for a fluid to be analysed, some examples of which are given later below.

Thirdly, the mounting plate 3 has a relatively large mass that helps to control the vibration characteristics as described further below.

The sensor probe 1 comprises a piece of insulating material 8 disposed inside the mounting ring 4 of the base 2 which provides a seal and prevents any mud from reaching the recess 5 and the electronic components 6 therein.

A pair of electrodes 15 are mounted in the piece of insulating material 8 so as to protrude from the base 2. Accordingly, the piece of insulating material 8 is disposed between the electrodes 15 and the base 2 to provide electrical insulation of the electrodes 15. The piece of insulating material 8 may be made of any material that provides suitable insulating and structural properties, for example PTFE (polytetrafluoroethylene).

The piece of insulating material 8 also reduces vibrational coupling as described further below. The electrodes 15 are made of metal and connected to the electronic components 6 by electrical connections (not shown) passing through the piece of insulating material 8.

The electrodes 15 are shaped as flat plates extending parallel to each other with a gap 16 therebetween. Thus, the electrodes 15 for a capacitive sensor probe whose capacitance depends on the permittivity of any fluid surrounding the electrodes 15, in particular in the gap 16. As described below, in use, the electrodes 15 have electrically oscillations generated therein for measurement of EM properties of the fluid surrounding the electrodes 15.

The electrodes 15 are configured to provide have a suitable capacitance for taking the measurements needed to determine the complex electrical permittivity of the fluid at the desired frequencies, typically in a range from 1 Hz to 100 MHz. In examples for use with an oil-based drilling mud, the gap 16 may have a size in a range from 2 mm to 5 mm, for example 3.0 mm or 3.6 mm, which is sufficiently wide to avoid any problems caused by sub-mm sized rock particles becoming stuck on the electrodes 15 and blocking fluid flow when the sensor probe 1 is inserted in a flowing fluid. In this example, the length of the electrodes 15 (away from the piece 8 of insulating material, vertically in FIGS. 3 and 4) is 50 mm and the width of the electrodes 15 (horizontally in FIG. 4) is 18 mm. These dimensions, combined with the gap 16 of 2 mm to 5 mm, results in a typical capacitance value in a range from 50 to 100 pF when the electrodes 15 are immersed in a typical oil-based drilling mud.

In typical embodiments, the gap 16 may have a size in a range from 3.0 mm to 5.0 mm. The length and width of the electrodes 15 may be varied, although in typical embodiments the area of each electrode 15 may be in the range from 5 cm$^2$ to 20 cm$^2$ in order to provide the electrodes 15 with a suitable capacitance.

A pair of shield members 20 protrude from the base 2. The shield members 20 are formed integrally with the mounting ring 4 and so made of the same metal as the base 2. As such, the shield members 20 are electrically grounded via the base 2. The shield members 20 have a gap 21 therebetween in which the electrodes 15 are located. Thus, the shield members 20 are disposed outside the electrodes 15. As the shield members are electrically grounded, they form a screened enclosure around the electrodes 15 and provide EM shielding of the electrodes 15. This means that the EM measurements made by the electrodes 15 are not significantly affected by the surrounding environment, for example the presence of any surrounding metalwork, e.g. in a conduit in which the sensor probe 1 may be used, which thereby enhances the reliability of the measurements.

To enhance the EM shielding, the shield members 20 protrude from the base 2 further than the electrodes 15, although in general could protrude by the same distance. For the same reason, the shield members 20 have a lateral extent (i.e. laterally of the direction in which they protrude from the base 2) that is greater than the lateral extent of the electrodes 15.

As well providing EM shielding, the shield members 20 are arranged to be operable as a tuning fork by having mechanical vibrations generated therein which may be used for measurement of physical properties of the fluid into which the sensor probe 1 is inserted. As the vibrations are affected by physical properties of the fluid, such as density and viscosity, measurements of parameters of the vibrations, such as the resonance frequency and the Q factor may be used to provide measures of those physical properties.

The configuration (including length, lateral extent, thickness and shape, taking into account the material properties) of the shield members 20 is chosen to provide the shield members 20 with a mechanical resonance suitable for measuring the desired physical properties of the fluid. For example, in the case that the fluid is an oil-based drilling mud, the mechanical resonance frequency may typically be in the range from 100 Hz to 1 kHz, which is suitable to measure densities of a fluid from ~0.75 g/ml (typical for a light base oil) to ~2 g/ml (typical for a heavy drilling mud).

Besides the configuration of the shield members 20, the sensor probe 1 is designed as follows having regard to the vibrations.

The base 2 is formed to have a mass that is selected to control the vibration characteristics of the shield elements 20. Providing the base 2 with a relatively large mass, predominantly provided by the mounting plate 3, helps to control the vibrational characteristics. The mounting plate 3 is rigidly connected to the mounting ring 4 that forms the top of the tuning fork since the mounting plate 3, mounting ring 4 and shielding members 20 (which form the tuning fork tines) are machined from a single piece of metal.

However, the shield members 20 are connected to the base 2, in particular to the mounting ring 4 by a portion 34 having a smaller cross-sectional area than the shield members 20 themselves so as to reduce the vibrational coupling between the base 2 and the shield members 20.

In addition, the piece of insulating material 8, as well as electrically insulating the electrodes 15, also reduces vibrational coupling between the shield members 20 and the electrodes 15, helping to acoustically decouple the electrodes 15 from the tuning fork. The electrodes 15 will inevitably vibrate sympathetically when the shield members 20 are vibrated, and the coupling could complicate the vibrational analysis to extract parameters such as the resonance frequency and Q factor. By dampening the vibrations of the electrodes 15, this problem is reduced or may not occur significantly at all. The shield members 20 designed to have a resonance with a relatively low frequency and high Q factor, whereas the electrodes 15 are designed to have a resonance with a higher frequency, and lower Q factor. The resonances of the shield members 20 and the electrode 15 are designed to have resonant frequencies separated by as large a frequency gap as possible.

The shield members 20 also contain embedded temperature sensors 35, typically being thermistors, which enable the temperature of the fluid to be measured while the sensor probe 1 is used.

The electronics components 6 in the recess 5 include a transducer arrangement 22 that comprises a first transducer 23 that generates vibrations in the shield members 20 and a second transducer 24 that converts the generated vibrations into a detection signal.

In this example, the first and second transducers 23 and 24 are piezoelectric transducers that each comprise a stack of ceramic piezoelectric rings 25 cemented together. The number of piezoelectric rings 25 is chosen to provide the desired amplitude of vibration for the voltage selected for the drive signal. The first and second transducers 23 and 24 are bolted to the top of the mounting ring 4 by bolts 26 extending through the piezoelectric rings 25. Optionally, a compliant spring washer (not shown) may be provided between the head of the bolt 26 and the top piezoelectric ring 25.

An alternative method of attaching the first and second transducers 23 and 24 to the mounting ring 4 is to glue them, but variability in the glue joint thickness would cause variability in the coupling efficiency between the first and second transducers 23 and 24 and the mounting ring 4. Such a glue joint is also vulnerable to cracking due to the stresses caused by thermal and acoustic expansion and contraction.

When an alternating drive signal is applied to the first transducer 23, it expands and contracts along its length (compressing and expanding the spring washer, if present) and thereby generating vibrations which are communicated to the mounting ring 4 and hence generating vibrations in the shield members 20.

This method of exciting the vibrations has been chosen because it is simple, reproducible and reliable over the lifetime of the sensor probe 1. However, other transducer arrangements could be used instead. For example the first and second transducers 23 and 24 could comprise a stack of piezoelectric blocks of any shape.

The second transducer 24 operates in the reverse manner to the first transducer 23 by converting the vibrations generated in the shield members 20 into a detection signal that is used to detect parameters of the vibration such as frequency and amplitude.

As an alternative to the first and second transducers 23 and 24, the transducer arrangement could comprise a single transducer which fulfils both tasks of generating the vibrations and providing a detection signal. However, experiments have shown that the use of first and second transducers 23 and 24 gives a much higher quality resonance signal for processing.

The sensor probe 1 may have a modified construction that is illustrated in FIGS. 5 to 8. The modified construction of sensor probe 1 is the same as the construction of the sensor probe 1 shown in FIGS. 1 to 4 apart from the modifications described below. Thus, common elements are labelled by common reference numerals and the above description thereof applies equally to the modified construction of sensor probe 1, except for the modifications described below.

In the modified construction, the sensor probe 1 has a base 2 that comprises a mounting plate 3 and a mounting ring 4 that protrudes from the mounting plate 3. However, the mounting plate 3 is a separate component from the mounting ring 4 and is connected to the mounting ring by four mounting bolts 9 that screw into threaded holes 10 formed in the mounting ring 4.

The mounting plate 3 may be formed from metal, typically a stainless steel. Behind the mounting ring 4, the mounting plate 3 has a recess 5 which houses various electronic components 6 as described below.

In addition, the base 2 also includes an annular support ring 11 that extends around the mounting ring 4. The mounting plate 3 is loosely connected to the support ring 11 which is held in place around the mounting ring 4 by a flexible O-ring 12 fitting in a circular groove 13 that extends around the circumference of the mounting ring 4.

The sensor probe 1 comprises a piece of insulating material 8 disposed inside the mounting ring 4 and a pair of electrodes 15 mounted in the piece of insulating material 8 so as to protrude from the base 2. Both the pair of electrodes 15 and the piece of insulating material 8 are configured as described above.

The sensor probe 1 comprises a pair of shield members 20 protrude from the mounting ring 1. The mounting ring 1 and the shield members 20 are machined from a single piece of metal, typically a stainless steel. The shield members 20 are configured as described above.

The electronics components 6 in the recess 5 include a transducer arrangement 22 that comprises a first transducer 23 that generates vibrations in the shield members 20 and a second transducer 24 that converts the generated vibrations into a detection signal. In the modified construction, the first and second transducers 23 and 24 operate in the same manner as described above but are configured differently, as will now be described.

In the modified construction, the shield members 20 have rear portions 27 that extending rearwardly of a surface 29 of the base 2 from which the pair of shield members 20 protrude. The first and second transducers 23 and 24 are thus connected between the rear portions 27 of the shield members 20.

The first and second transducers 23 and 24 each comprises a stack of ceramic piezoelectric blocks 28 cemented together. The number of piezoelectric blocks 28 is chosen to provide the desired amplitude of vibration for the voltage selected for the drive signal.

Each of the first and second transducers 23 and 24 further comprises a metal sleeve 33 inside which the stack of piezoelectric blocks 28 is disposed and a screw bolt assembly 30 that holds the stack of piezoelectric blocks 28 in place between the rear portions 27 of the shield members 20 and allows the compression of the piezoelectric blocks 28 between the shield members 20 to be controlled and adjusted. The rear portions 27 of the shield members 20 are each separated into two halves 31 by vertical slits 32, the first and second transducers 23 and 24 being respectively connected to different halves 31. This allows the compression of the piezoelectric blocks 28 of the first and second transducers 23 and 24 to be adjusted independently.

The first and second transducers 23 and 24 are operated in the same manner as described above, but the modified construction has been found to improve the coupling efficiency of vibrations between the first and second transducers 23 and 24 and the shield members 20, as compared to the construction of the sensor probe 1 shown in FIGS. 1 to 4. The vibrational coupling efficiency is improved for both driving of vibrations by the first transducer 23 and detection of vibrations by the second transducer, and is acheived because the first and second transducers 23 and 24 are connected between the shield members 20. Therefore the construction of the sensor probe 1 shown in FIGS. 1 to 4 is effective, but the modified construction of the sensor probe 1 shown in FIGS. 5 to 8 provides better performance.

Figure 9:
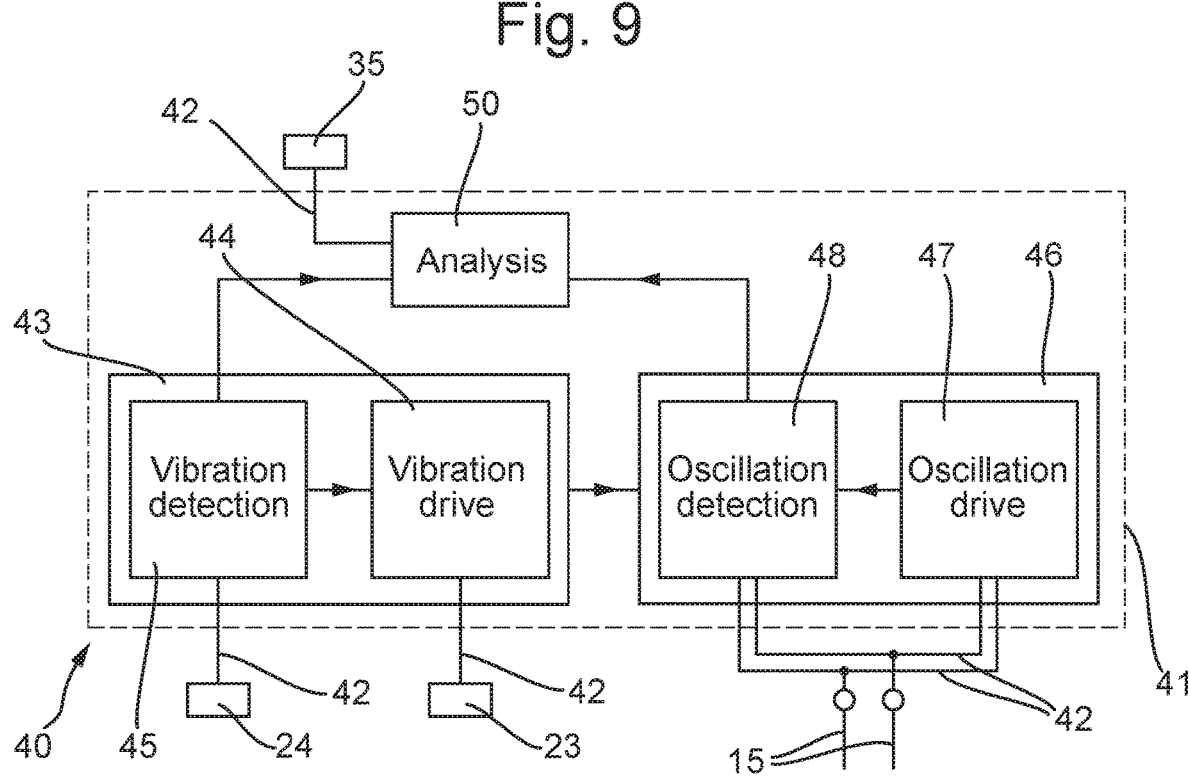
FIG. 9 is a diagram of the circuit arrangement of the sensor probe.

The sensor probe 1 includes an electrical circuit 40 that is used to control the operation of the sensor probe 1. The electrical circuit 40 is shown in FIG. 9 and may be housed in a screened enclosure 41 which may have any suitable form and construction. The enclosure 41 may be mounted to the base 2 of the sensor probe 1. The electrical circuit 40 may be connected to the electrodes 15, to the first and second transducers 23 and 24, and to the temperature sensors 35 by flexible wire connections 42.

The electrical circuit 40 includes a vibration section 43 for the shield members 20 which comprises a vibration drive circuit 44 and a vibration detection circuit 45.

The vibration drive circuit 44 is connected to the first transducer 23 and supplies a vibration drive signal thereto. The vibration drive signal causes the first transducer 23 to generate vibrations as described above.

The vibration detection circuit 45 is connected to the second transducer 24 and detects one or more parameters of the generated vibrations from the detection signal output by the second transducer. The parameters may include any one or more of the resonant frequency, the amplitude of the oscillations, the Q factor of the vibrations, or any other parameter. The vibration drive signal has a frequency selected to provide vibrations at the mechanical resonance frequency of shield members. Typically, the frequency of the vibration drive signal may be in the range from 100 Hz to 1 kHz. The vibration detection circuit 45 may comprise suitable electrically components and processing units which may be dedicated hardware or a microprocessor running an appropriate program.

The electrical circuit 40 includes an EM section 46 for the electrodes 15 which comprises an oscillation drive circuit 47 and an oscillation detection circuit 48.

The oscillation drive circuit 47 supplies an oscillation signal to the electrodes 15 which generates electrical oscillations between the electrodes 15. The oscillation signal has a frequency selected for measuring an EM property of interest. Typically, the frequency of the oscillation signal is in a range from 1 Hz to 100 MHz.

The oscillation detection circuit 48 is also connected to the electrodes and detects one or more parameters of the generated electrical oscillations. The parameters may include any one or more of the frequency of the oscillations, the amplitude of the oscillations, the Q factor of the oscillations, or any other parameter. The oscillation detection circuit 48 may comprise suitable electrically components and processing units which may be dedicated hardware or a microprocessor running an appropriate program.

Additional advantage is achieved by the vibration drive circuit 44 also supplying the vibration drive signal to the oscillation detection circuit 48 which then detects the one or more parameters of the generated electrical oscillations synchronously with the vibration drive signal. While the geometry of the electrodes 15 and their mounting arrangement has been chosen to reduce acoustic coupling so that any induced vibrational coupling of the electrodes does not significantly compromise the resonance of the shield members 20. However, the induced vibration does have the effect of modulating the electrical response of the electrodes 15 at the frequency of the vibrations, because the vibrations modulate the coupling to ground of the electrodes 15 and hence modulate the voltage measured between the two electrodes 15. Thus, by synchronously detecting the generated electrical oscillations synchronously with the vibration drive signal as the reference, the sensitivity of the detection can be considerable improved over a non-synchronous measurement by the resulting improvement in the signal-to-noise ratio.

One of the benefits of the combined measurement function of the sensor probe 1 is that the vibration of the shield members 20 also reduces the build-up of any material deposits on the surfaces of the sensor probe 1. This is a particular benefit when the probe is permanently inserted in a conduit or a container. To further enhance this effect of removing material deposits from the sensor probe, the shield members 20 are periodically vibrated with greater energy. This may be achieved by the vibration drive circuit 44 periodically supplying a cleaning drive signal of greater power than the vibration drive signal.

The sensor probe 1 also includes an analysis system 50 that is supplied with the one or more parameters of the generated electrical oscillations and with the one or more parameters of the generated vibrations, and performs an analysis thereof, as follows. The analysis system 50 may be any form of circuit that is capable of performing the analysis, for example dedicated hardware or a microprocessor running an appropriate program. In particular, the analysis system 50 derives a measure of at least one EM property of the fluid from the one or more parameters of the generated electrical oscillations. The analysis system 50 also derives a measure of at least one physical property of the fluid from the one or more parameters of the generated vibrations.

The principles underlying the operations performed in the vibration detection circuit 45, the oscillation detection circuit 48 and the analysis system 50 are known in themselves, but a specific non-limitative example is as follows.

The oscillation drive circuit 47 may generate the oscillation drive signal as an alternating current at a selected frequency via a frequency synthesis chip. The oscillation drive signal, as well as being supplied to electrodes 15, is supplied to the oscillation detection circuit 48 which passes it through a reference resistor R and measures the voltage $V_R$ across the resistor determined as a reference signal. The oscillation detection circuit 48 detects the voltage $V_S$ across the electrodes 15 as the sample signal and then derives EM parameters that are the magnitude of the fluid impedance |Z| and the phase angle $\varphi$ from $V_R$ and $V_S$.

If the fluid is represented as a parallel combination of a capacitance C and resistance R, the values of these parameters can be calculated for frequency $f=\omega/(2\pi)$ from the fluid impedance using the following equations.

$$C=-\tan(\varphi)/(\omega R)$$

$$R=|Z|\cdot\sqrt{((1+\tan(\varphi)^2)}$$

For the case of an oil-based drilling mud, typically the capacitance is measured to an accuracy of ±0.1 pF.

From these parameters of the generated electrical oscillations, the analysis system 50 derives a measure of the complex permittivity of the fluid, which is the EM property in this example. The capacitance C is linearly proportional to the real part of the fluid permittivity, with a proportionality constant that can be determined by calibrating the probe in a range of standard dielectric fluids, as detailed for example in Gregory and Clarke, "Tables of the Complex Permittivity of Dielectric Reference Liquids at frequencies up to 5 GHz", National Physical laboratory Report MAT 23 Jan. (2012). The resistance is inversely proportional to the fluid conductivity, with a proportionality constant that can be determined by calibrating the probe in a range of standard solutions (e.g. sodium chloride or calcium chloride solutions with different molarities).

The main difficulties with the permittivity measurement lie in the accurate extraction of |Z| and $\varphi$ from the values of $V_R$ and $V_S$ since the phase shifts can be very small, of the order of a few thousandths of a degree. There are several possible methods of doing this, but a phase measurement accuracy of circa 0.001° is required which is challenging. For this reason, the improved sensitivity achieved by the vibration induced in the electrodes having the effect of modulating the electrical response of the electrodes, and the synchronous detection which can therefore be used, is highly advantageous.

The sensor probe 1 is capable of measuring the real part of the complex permittivity of a water-based mud at relatively high frequencies of, say, 1 MHz or greater.

However, further modification is needed to measure the real part of the complex permittivity of a water-based mud at much lower frequencies down to a few Hz. This information would be needed to compute the composition of the water-based mud in an analogous procedure to that used for oil-based muds.

The low frequency problem is due to the electrode polarization effects that occur when the salt ions in the brine form a capacitive barrier layer at the surfaces of the two electrodes, blocking the low frequency current flow. To overcome this, the sensor probes 1 may be modified to include an additional pair of electrodes (not shown) outside the existing pair of electrodes 15 to allow measurement of the true capacitance and resistance of the sample. In that case, the additional pair of electrodes is used to inject the current into the fluid and the additional pair of electrodes is used to measure the phase and amplitude of the voltage. If the circuit impedance is made high enough, no current flows into and out of the electrodes and so a capacitive barrier layer does not form. In this case, the size of the sensor probe 1 increases. In addition, the width of the inner pair of electrodes 14 must be reduced in order to perturb the current flow between the outer pair of electrodes as little as possible.

The vibration drive circuit 44 may generate the vibration drive signal as an alternating voltage at a selected frequency via a frequency synthesis chip. This vibration drive signal is amplified, and then supplied to the first transducer 23 to induce vibrations in the shield members 20. These vibrations cause a voltage to be generated in the second transducer 24 to be generated as a detection signal. The vibration detection circuit 45 derives parameters of amplitude and phase of this detection signal, relative to the amplitude and phase of the vibration drive signal which is supplied from the vibration drive circuit 44. The vibration drive signal is swept through the resonance value, and the detection signal is analysed to determine the physical parameters of the resonance frequency and the Q factor.

The analysis system 50 derives a measure of the density and viscosity of the fluid, which are the physical properties in this example, the density being derived from the resonant frequency and the viscosity being derived from the Q factor, in a manner which is known in itself. For the case of an oil-based drilling mud, typically the density of the fluid ranges between ~0.7 g/ml (typical for a typical synthetic base oil) to 2 g/ml (typical for a heavy drilling mud) and the density is measured to an accuracy of ±0.01 g/ml.

The analysis system 50 may implement the analytical model describing the relationship between tuning fork parameters and the mud density and viscosity that has been described in Heinisch et al., "Reduced order models for Resonant Viscosity and Mass Density Sensors", Sensors and Actuators A: Physical, Vol. 220, 1 Dec. 2014, pp. 76-84. This paper calculates the form of the equations relating the resonance frequency $f_M$ and Q factor $Q_M$ to the fluid density $\rho_M$ and viscosity $\eta_M$ according to the following equations:

$$2\pi\cdot f_M=1/(a1+a2\cdot\rho_M+a3\cdot(\rho_M\cdot\eta_M/(2\pi\cdot f_M))^{1/2})^{1/2}$$

$$2\pi\cdot f_M\cdot Q_M=1/(b1+b2\cdot\eta_M+b3\cdot(2\pi\cdot f_M\cdot\rho_M\cdot\eta_M)^{1/2})^{1/2}$$

These equations contain 6 scalar parameters a1, a2, a3, b1, b2 and b3 which can be determined by calibrating the instrument in (at least) three different fluid samples with known density and viscosity values.

The analysis system 50 is supplied with the output signal from the temperature sensors 35 representing the measured temperature of the fluid, and may adapt the analysis performed thereby on the basis thereof.

The sensor probe may be used to measure a range of fluids, including the following non-limitative examples.

One fluid of particular interest is an oil-based drilling mud. Drilling muds consist of a mixture of oil (either a synthetic base oil or diesel), brine (usually containing calcium chloride or sodium chloride), and solid materials such as clays and drilling rock. The key feature as far as the electrical properties are concerned it that the oil forms the continuous matrix within which isolated brine droplets and isolated solid particles are dispersed. This type of mud exhibits a very low electrical conductivity at DC.

Another fluid which may be analysed is a water-based drilling mud, the brine forms the continuous matrix within which isolated oil droplets and isolated solid particles are dispersed. This type of mud exhibits a high electrical conductivity at DC, once electrode polarization effects are accounted for.

The sensor probe may be used to measure a fluid in a range of test environments.

In one example, the sensor probe 1 may measure a static sample of fluid, for example a sample that has been extracted from an oil and gas operation for testing in a laboratory. This may be referred to as a dip probe. In this case, the electrodes and shield members may be inserted into the static sample of the fluid.

Figure 10:
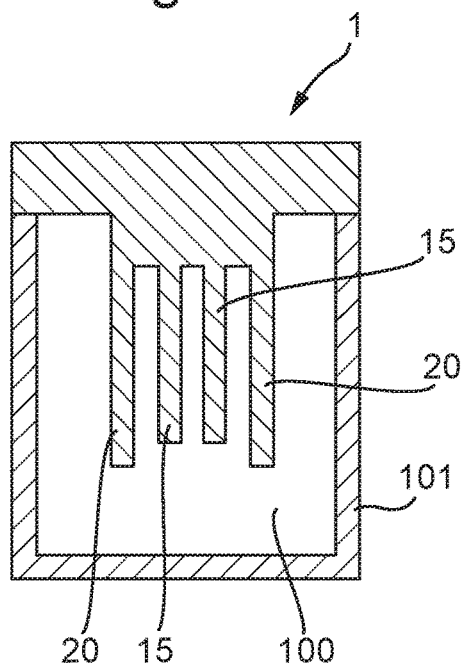
FIG. 10 is a cross-sectional view of the sensor probe inserted into a test pot.

FIG. 10 illustrates an example of a sensor probe that is a dip probe. In this example, a static sample of the fluid 100 has been disposed in a test pot 101 which may be for example a conventional test pot of volume 200 ml or comparable sized laboratory beaker. The base 2 of the sensor probe 1 is designed to fit the opening of the test pot 101. Thus, the sensor probe 1 is introduced into the test pot 101 with the electrodes 15 and the shield members 20 inserted and completely immersed in the sample of fluid 100 without touching or being very close to the walls or base of the test pot 101. Once inserted, the sensor probe 1 is operated to take measurements as described above.

Figure 11:
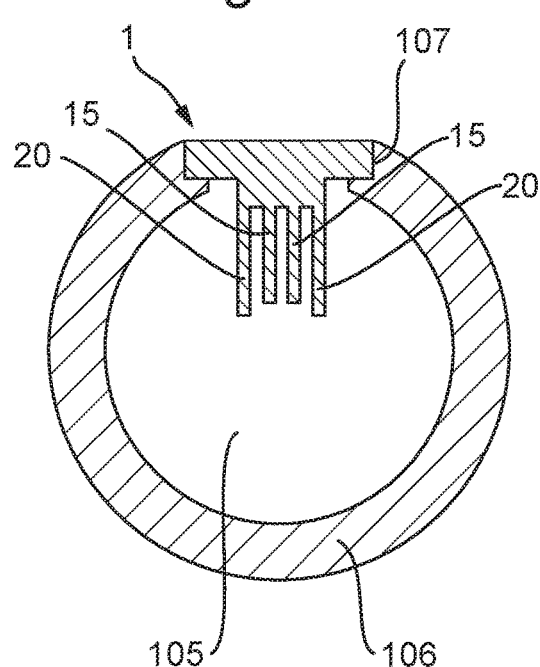
FIG. 11 is a cross-sectional view of the sensor probe inserted into a pipe, the cross-section being taken across the pipe.

In another example, the sensor probe 1 may measure a flowing fluid, for example a fluid flowing in a conduit such as a pipe. This may be referred to as a pipe probe. In that case, the electrodes and shield members may be inserted into the interior of the conduit where the fluid is flowing. FIG. 11 shows an example of a sensor probe 1 that is a pipe probe. In this example, a fluid 105 is flowing in a pipe 106. The pipe 106 has an opening 107 for permitting insertion of the sensor probe 1 and the base 2 of the sensor probe 1 is designed to fit the opening 107. The sensor probe 1 may be permanently mounted in the pipe 106 or periodically fitted to the pipe 106 for taking measurements. Thus, the sensor probe 1 is introduced into the pipe 106 with the electrodes 15 and the shield members 20 inserted in the flowing fluid 105 without touching or being very close to the walls of the pipe 106. Once inserted, the sensor probe 1 is operated to take measurements as described above.

The sensor probe 1 is designed so that it permits the continued flow of fluid 105 through the pipe 106. In this regard, the gap 21 between the shield members 20 has the advantage, compared to an annular shield member of improving the flow of fluid 105 past the sensor probe 1 with minimal obstruction of the cross-section of the pipe 106. To minimise the obstruction, in the arrangement shown in FIG. 11 the sensor probe 1 is be inserted with the gap 21 between the shield members 20 arranged in line with the direction of flow of the fluid 105 (into the paper in FIG. 11).

The sensor probe 1 may have essentially the same construction for any application. The sensor probe 1 may be adapted to fit with the container for the fluid, for example the pot 101 or the pipe 106 in the above examples. This may involve adaption of the shape of the mounting plate 2 and/or design of the enclosure 41 for the electronic circuit 40.

The invention claimed is:

1. A sensor probe for analysis of a fluid, the sensor probe comprising
a base,
a pair of electrodes and a pair of shield members protruding from the base for insertion into the fluid, the electrodes being configured to have electrical oscillations generated therein for measurement of electromagnetic properties of a fluid surrounding the electrodes and the shield members being disposed outside the electrodes for electromagnetically shielding the electrodes and being configured to have vibrations generated therein for measurement of physical parameters of the fluid, and
a transducer arrangement comprising at least one transducer arranged to generate the vibrations in the shield members and to convert the generated vibrations into a detection signal.

2. A sensor probe according to claim 1, wherein the at least one transducer includes a first transducer arranged to generate the vibrations in the shield members and a second transducer arranged to convert the generated vibrations into a detection signal.

3. A sensor probe according to claim 1, wherein the at least one transducer is a piezoelectric transducer.

4. A sensor probe according to claim 1, wherein the at least one transducer is connected between the pair of shield members.

5. A sensor probe according to claim 4, wherein the shield members have rear portions extending in an opposite direction to the pair of shield members from the base from which the pair of shield members protrude, the at least one transducer connected between the rear portions of the shield members.

6. A sensor probe according to claim 1, further comprising
a vibration drive circuit connected to the transducer arrangement and arranged to supply a vibration drive signal thereto, and
a vibration detection circuit connected to the transducer arrangement and arranged to detect one or more parameters of the generated vibrations from the detection signal.

7. A sensor probe according to claim 6, further comprising an analysis system supplied with the one or more parameters of the generated vibrations and arranged to derive a measure of at least one physical property of the fluid therefrom.

8. A sensor probe according to claim 6, wherein the vibration drive circuit is further arranged to supply a cleaning drive signal of greater power than the vibration drive signal for removal of material deposits on the probe.

9. A sensor probe according to claim 1, further comprising an oscillation drive circuit connected to the electrodes and arranged to supply an oscillation signal for generating the electrical oscillations between the electrodes, and an oscillation detection circuit arranged to detect one or more parameters of the generated electrical oscillations.

10. A sensor probe according to claim 9, further comprising
a vibration drive circuit connected to the transducer arrangement and arranged to supply a vibration drive signal thereto, and
a vibration detection circuit connected to the transducer arrangement and arranged to detect one or more parameters of the generated vibrations from the detection signal, wherein
the oscillation drive circuit is arranged to supply the oscillation signal to the electrodes at the same time as the vibration drive circuit supplies the vibration drive signal to the transducer arrangement.

11. A sensor probe according to claim 10, wherein the oscillation detection circuit is arranged to detect said one or more parameters of the generated electrical oscillations synchronously with the vibration drive signal.

12. A sensor probe according to claim 9, wherein the oscillation signal has a frequency in a range from 1 Hz to 100 MHz.

13. A sensor probe according to claim 9, further comprising an analysis system supplied with the one or more parameters of the generated electrical oscillations and arranged to derive a measure of at least one electromagnetic property of the fluid therefrom.

14. A sensor probe according to claim 1, wherein the shield members are connected to the base by a portion having a smaller cross sectional area than the shield members for reducing vibrational coupling between the base and the shield members.

15. A sensor probe according to claim 1, wherein the sensor probe further comprises a piece of electrically insulating material disposed between the electrodes and the base and arranged to reduce vibrational coupling between the shield members and the electrodes.

16. A sensor probe according to claim 1, wherein the shield members have a greater lateral extent than the electrodes.

17. A sensor probe according to claim 1, wherein the shield members protrude from the base at least as far as the electrodes.

18. A sensor probe according to claim 1, wherein the shield members have a mechanical resonance frequency in the range from 100 Hz to 1 kHz.

19. A method of using a sensor probe, the sensor probe comprising a base, and a pair of electrodes and a pair of shield members protruding from the base for insertion into the fluid, the electrodes being configured to have electrical oscillations generated therein for measurement of electromagnetic properties of a fluid surrounding the electrodes and the shield members being disposed outside the electrodes for electromagnetically shielding the electrodes and being configured to have vibrations generated therein for measurement of physical parameters of the fluid, the method comprising:

inserting the electrodes and shield members into a fluid, generating electrical oscillations in the electrodes and taking a measurement of at least one electromagnetic property of the fluid from the generated electrical oscillations, and vibrating the shield members and taking a measurement of at least one physical property of the fluid from the generated vibrations.

20. A method according to claim 19, wherein the step of generating electrical oscillations in the electrodes and taking a measurement of at least one electromagnetic property of the fluid from the generated electrical oscillations, is performed simultaneously with the step of vibrating the shield members and taking a measurement of at least one physical property of the fluid from the generated vibrations.

21. A method according to claim 19, wherein the fluid is a flowing fluid.

22. A method according to claim 19, wherein in the step of inserting a gap between the shield members is arranged in line with the direction of flow of the fluid.

23. A method according to claim 19, wherein the fluid is an oil-based drilling mud.

* * * * *